United States Patent [19]
Sherman et al.

[11] Patent Number: 6,117,851
[45] Date of Patent: Sep. 12, 2000

[54] TREATMENT OF OSTEOARTHRITIS BY ADMINISTERING POLY-N-ACETYL-D-GLUCOSAMINE

[75] Inventors: William T. Sherman, Hendersonville, N.C.; Robert W. Gracy, Fort Worth, Tex.

[73] Assignee: Lescarden Inc., New York, N.Y.

[21] Appl. No.: 08/990,161

[22] Filed: Dec. 12, 1997

Related U.S. Application Data

[60] Provisional application No. 60/032,855, Dec. 13, 1996.

[51] Int. Cl.$^7$ .................................................. A61K 31/70
[52] U.S. Cl. ............................................................. 514/62
[58] Field of Search ................................................. 514/62

[56] References Cited

U.S. PATENT DOCUMENTS

| | | |
|---|---|---|
| 3,632,754 | 1/1972 | Balassa . |
| 3,683,076 | 8/1972 | Rovati . |
| 3,697,652 | 10/1972 | Rovati et al. . |
| 3,903,268 | 9/1975 | Balassa . |
| 3,911,116 | 10/1975 | Balassa . |
| 3,914,413 | 10/1975 | Balassa . |
| 4,473,551 | 9/1984 | Schinitsky . |
| 5,192,750 | 3/1993 | Burton et al. . |
| 5,587,363 | 12/1996 | Henderson . |

OTHER PUBLICATIONS

Vajaradul, Y., *Clinical Therapeutics*, 3(5):336–343, 1981.
D'Ambrosio, E. et al., *Pharmatherapeutica* 2(8):1981.
Pujalte, José M. et al., *Current Medical Research and Opinion* 7(2):110–114, 1980.
Vaz, Antonio Lopes, *Current Medical Research and Opinion* 8(3):145–149, 1982.
Crolle, G. et al., *Current Medical Research and Opinion* 7(2), 1980.
Vajranetra, P., *J. Med. Ass. Thailand* 67(7):409–418, 1984.
Chitin and Chitosan: General Properties and Applications, pp. 1–8, Vansou, DuPont Brochure.
van Ornum, Joel, *Infofish Int'l.*, Jun. 1992:48–52, Nov./Dec., 1992.
Kamel, M. et al., *Clinical and Experimental Rheumatology* 9:17–21, 1991.
Sato, H. et al., *Arithritis and Rheumatism* 31(1):63–71, Jan. 1988.

*Primary Examiner*—Zohreh Fay
*Attorney, Agent, or Firm*—Darby & Darby

[57] ABSTRACT

The methods of the present invention relate to administering to a mammal afflicted with osteoarthritis an effective amount of poly-N-acetyl-D-glucosamine (poly-NAG), partially depolimerized poly-NAG, pharmaceutically acceptable salts of poly-NAG, or mixtures thereof, to treat osteoarthritis and/or alleviate the symptoms of osteoarthritis such as pain, joint tenderness and swelling and impaired joint mobility. The present invention also comprises solid and liquid pharmaceutical dosage forms comprising poly-NAG, its pharmaceutically acceptable salts and mixtures thereof. These dosage forms may be administered orally and by-injection to treat osteoarthritis and/or alleviate the symptoms thereof.

16 Claims, 1 Drawing Sheet

TREATMENT OF OSTEOARTHRITIS BY ADMINISTERING POLY-N-ACETYL-D-GLUCOSAMINE

This application claims priority pursuant to 35 U.S.C. §119 from U.S. Provisional Application Ser. No. 60/032,855 filed Dec. 13, 1996, the entire disclosure of which is hereby incorporated by reference.

FIELD OF THE INVENTION

This invention relates to methods for treating osteoarthritis in mammals using pharmaceutical formulations comprising poly-N-acetyl-D-glucosamine (poly-NAG), a pharmaceutically acceptable derivative of poly-NAG, or mixtures thereof. The invention also relates to solid and liquid pharmaceutical dosage forms for oral and by-injection administration of poly-NAG and its derivatives.

BACKGROUND OF THE INVENTION

Osteoarthritis is a degenerative joint disease affecting articular cartilage developing in the fourth and fifth decades of life that was initially believed to be a disease of wear and tear due to mechanical stress on the joints. It is now known that the pathology of osteoarthrosis is not entirely mechanical and involves changes in the joint metabolism. Specifically, altered glucosamine metabolism appears to play a key role in the development of osteoarthritis.

An effective treatment of osteoarthritis must address two types of problems: (i) pain, and joint tenderness, swelling and stiffness must be alleviated as an immediate patient's problem; and (ii) the degenerative process must be stopped preferably at its earlier stages. Treatment with anti-rheumatics and nonsteroidal anti-inflammatory drugs has not proven successful. Anti-rheumatics, although quickly effective, were recently shown to impair the very function that physicians were trying to improve, and anti-inflammatory drugs alleviate the pain but do not address the underlying degenerative disorder.

Recent biochemical and pharmacological studies have suggested a novel and more effective treatment of osteoarthritis. These studies have shown that administration of glucosamine tends to normalize cartilage metabolism, inhibiting degradation, and stimulating the synthesis of proteoglycans resulting in partial restoration of the articular function. The therapeutic effectiveness of a treatment with glucosamine has been demonstrated in a number of animal and human studies.

Glucosamine is a building block of the ground substance of the articular cartilage, the proteoglycans. Glucosamine is also the preferential substrate and a stimulant of proteoglycan biosynthesis. Furthermore, glucosamine inhibits the degradation of proteoglycans and rebuilds the experimentally damaged cartilage. Based on these findings, different types of glucosamine were introduced in the therapy of osteoarthritis. The clinical experience with preparations containing glucosamine derivatives confirmed the efficacy and the safety of the glucosamine treatment. The following is a brief summary of recent developments concerning the use of glucosamine sulfate to treat osteoarthritis.

Glucosamine sulfate is an artificially synthesized salt of glucosamine. Based on animal models, glucosamine sulfate has the potential to slow the degeneration of cartilage by stimulating cartilage cells to synthesize glucosamine, glycans and proteoglycans, the building components of cartilage. See Setnikar et al., *Anti-Arthritic Effects of Glucosamine Sulfate Studied in Animal Models*, Drug Research, 41:542–549 (1991). This study has also reported that glucosamine sulfate has anti-inflammatory properties by acting through a mechanism that inhibits the activity of proteolytic enzymes.

In the early 1980s, a number of small controlled human trials were conducted to study the clinical use of glucosamine sulfate in the treatment of osteoarthritis. Scientists evaluated glucosamine sulfate both as a symptomatic treatment and as a basic therapy to slow the underlying degenerative process. See Vaz, A. L., *Double Blind Clinical Evaluation of the Relative Efficacy of Ibuprofen and Glucosamine Sulfate in the Management of Osteoarthritis of the Knee in Out-patients*, Curr. Med. Res. Opin., 8:145–149 (1982); Vajaradul, Y., *Double Blind Clinical Evaluation of Intra-Articular Glucosamine in Outpatients with Gonarthrosis*, Clin. Therapeutics, 3:336–343 (1981); Pujalte, A.M., et al., *Double Blind Clinical Evaluation of Oral Glucosamine Sulfate in the Basic Treatment of Osteoarthrosis*, Curr. Med. Res. Opin., 7:1010–1014 (1980); Crolle, G. and D'Este, E., *Glucosamine Sulfate for the Management of Arthrosis: A Controlled Clinical Investigation*, Curr. Med. Res. Opin., 7:104–109 (1980).

These studies have shown that administration of glucosamine sulfate produces significant improvement in the symptoms of pain, joint tenderness, swelling and mobility. In addition, the treatment helped restore the patients' cartilage. Furthermore, the treatment was shown not to have any adverse side effects or undesirable interactions with other drugs normally used by elderly arthritic patients.

Glucosamine sulfate can be administered by interarticular, intramuscular and intravenous injection as well as orally. See D'Ambrosio et al., In *Glucosamine Sulfate: a Controlled Clinical Investigation in Arthrosis*, Pharmatherapeutica, 2:504–508 (1981). Vagaradul, Y., Clin. Therapeutics, 3:336–343 (1981), has reported a combination treatment using both intramuscular and oral administration. In all reported clinical trials oral glucosamine sulfate was administered at 1.5 g/day. For example, Pujalte teaches administration of 500 mg of glucosamine sulfate three times a day for a period of 6 to 8 weeks. Crolle teaches administration of one intramuscular injection of glucosamine sulfate (400 mg/day) for 7 days followed by oral administration of 500 mg of glucosamine sulfate three times a day for a period of 14 days. Vaz discloses an 8 week treatment by oral administration of 500 mg of glucosamine sulfate three times a day. The dose of 1.5 g glucosamine sulfate is equivalent to about one gram of D-glucosamine base.

The bioavailability of glucosamine was studied extensively. A number of studies reported the pharmacokinetics, organ distribution, metabolism and excretion of glucosamine. The studies were done in dog, rat and man. See Setnikar, I., et al., *Pharmacokinetics of Glucosamine in the Dog and Man*, Arzneim-Forsch/Drug Res. 36:729-35 (1986); Setnikar, I. et al., *Absorption, Distribution and Excretion of Radioactivity After a Single Intravenous or Oral Administration of [14]C Glucosamine to the Rat*, Pharmatherapeutica, 3:538–50 (1984); Levin, R. et al., *Glucosamine and Acetyl-Glucosamine Tolerance in Man*; J. Lab. Clin. Med, 59:927–931 (1961); Gaulden, E. C. and Keating, W. C., *The Effect of Intravenous N-acetyl-D-Glucosamine on the Blood and Urine Sugar Concentration of Normal Subjects*, Metabolism, 13:466–472 (1964); Kohn P. et al., *Metabolism of D-Glucosamine and N-acetyl-D-Glucosamine in the Intact Rat*, J. Bio. Chem., 237:304–307 (1962); Weiden, S. and Wood, I.J., *The Fate of Glucosamine Hydrochloride Injected Intravenously in Man*, J. Clin. Path. 11:343–349 (1958).

These studies have shown that glucosamine is found in the plasma immediately after intravenous administration, from where it readily diffuses into organs and tissues. See Setnikar et al. (1986). In both dog and man, glucosamine disappears quickly from plasma, usually after 30 to 60 minutes, and gets incorporated into α and β globulins. The protein incorporation of glucosamine reaches a peak after 8 hours and slowly disappears, having a half-life of 2.9 days. The glucosamine is excreted 34% in urine mainly as glucosamine and 1.7% in the feces. It is also degraded and excreted as $CO_2$. The liver and kidney show significant incorporation of glucosamine. In addition, the articular cartilage shows an active uptake. Setnikar also teaches that the distribution of glucosamine after oral administration is similar to the distribution after the intravenous administration. In addition, these studies have shown that N-acetyl-D-glucosamine (NAG) metabolizes in the body to glucosamine.

Other studies have also shown that the half-life of glucosamine in the blood is relatively short due to its degradation and/or incorporation into other bodily compounds. See Gaulden and Keating; Weiden et al.; and Levin et al. Accordingly, it is difficult to maintain adequate therapeutic levels in vivo which requires prolonged treatments and multiple daily administrations.

It has now been surprisingly discovered that poly-N-acetyl-D-glucosamine (poly-NAG), can be used as a source of glucosamine to treat osteoarthritis and/or alleviate symptoms thereof. This is surprising since it is generally known that poly-NAG is highly resistant to chemical attack except that of a most drastic nature. Furthermore, it was surprisingly discovered that individuals who ingest poly-NAG have higher serum levels of NAG and glucosamine. Poly-NAG maintains these serum levels for a longer period of time than when NAG is ingested alone and therefore provides a longer lasting source of glucosamine for the treatment of osteoarthritis. Thus, treatment with poly-NAG offers unexpected advantages over the prior art treatments with glucosamine and NAG.

In addition, poly-NAG, which need not be highly refined and purified, is considerably cheaper than glucosamine and NAG. According to the 1995 Sigma Chemical Company catalogue, the price of poly-NAG (chitin) is $55/kg, while glucosamine and NAG cost $86/kg and $391/kg, respectively. Commercial quantities of poly-NAG suitable for ingestion may be obtained at an even lower price ($25/kg). Accordingly, treatment with poly-NAG also offers the cost advantages over the prior art treatments with glucosamine and NAG.

BRIEF DESCRIPTION OF THE INVENTION

It has now been surprisingly discovered that poly-N-acetyl-D-glucosamine (poly-NAG) can be used to treat osteoarthritis. Furthermore, it has also been surprisingly discovered that individuals who ingest poly-NAG have higher serum levels of NAG and glucosamine for a longer period of time than the individuals who ingest a comparable amount of NAG alone. Poly-NAG thus increases the observed time that NAG and glucosamine remain in the serum and accordingly provides clinically proven beneficial therapeutic properties of glucosamine for a longer period of time. Thus, treatment of osteoarthritis with poly-NAG is superior to the treatment with glucosamine or NAG taught by the prior art.

One object of the present invention is to provide a method for treating osteoarthritis in mammals by administering to a mammal in need of such treatment an effective amount of poly-NAG for treatment of osteoarthritis.

Another object of the present invention relates to a method of alleviating the symptoms of osteoarthritis in mammals, such as pain, joint tenderness and swelling, and impaired joint mobility, by administering poly-NAG to a mammals having such symptoms in an amount effective to alleviate at least one of the symptoms of osteoarthritis.

A further object of the invention is to provide a method of treating osteoarthritis and/or alleviating the symptoms thereof in mammals by administering orally poly-NAG, its pharmaceutically acceptable salts, or mixtures thereof, to a mammal in need of such treatment in an amount effective to treat osteoarthritis and/or alleviate the symptoms thereof.

A still further object of the invention is to provide a method of treating osteoarthritis and/or alleviating the symptoms thereof in mammals by injecting a mammal in need of such treatment with poly-NAG, its pharmaceutically acceptable salts, or mixtures thereof, in an amount effective to treat osteoarthritis and/or alleviate the symptoms thereof. The injection may be intravenous, intramuscular, intra-articular or subcutaneous.

Yet another object of the invention relates to a method of treating osteoarthritis and/or alleviating the symptoms thereof by combining the oral and by-injection administrations of poly-NAG.

An additional object of the invention relates to solid and liquid dosage forms containing poly-NAG, its pharmaceutically acceptable salts, or mixtures thereof, and adapted for oral or by-injection administration.

These and other objects of the present invention will be apparent from the detailed description of the invention.

DETAILED DESCRIPTION OF THE INVENTION

Figure 1:
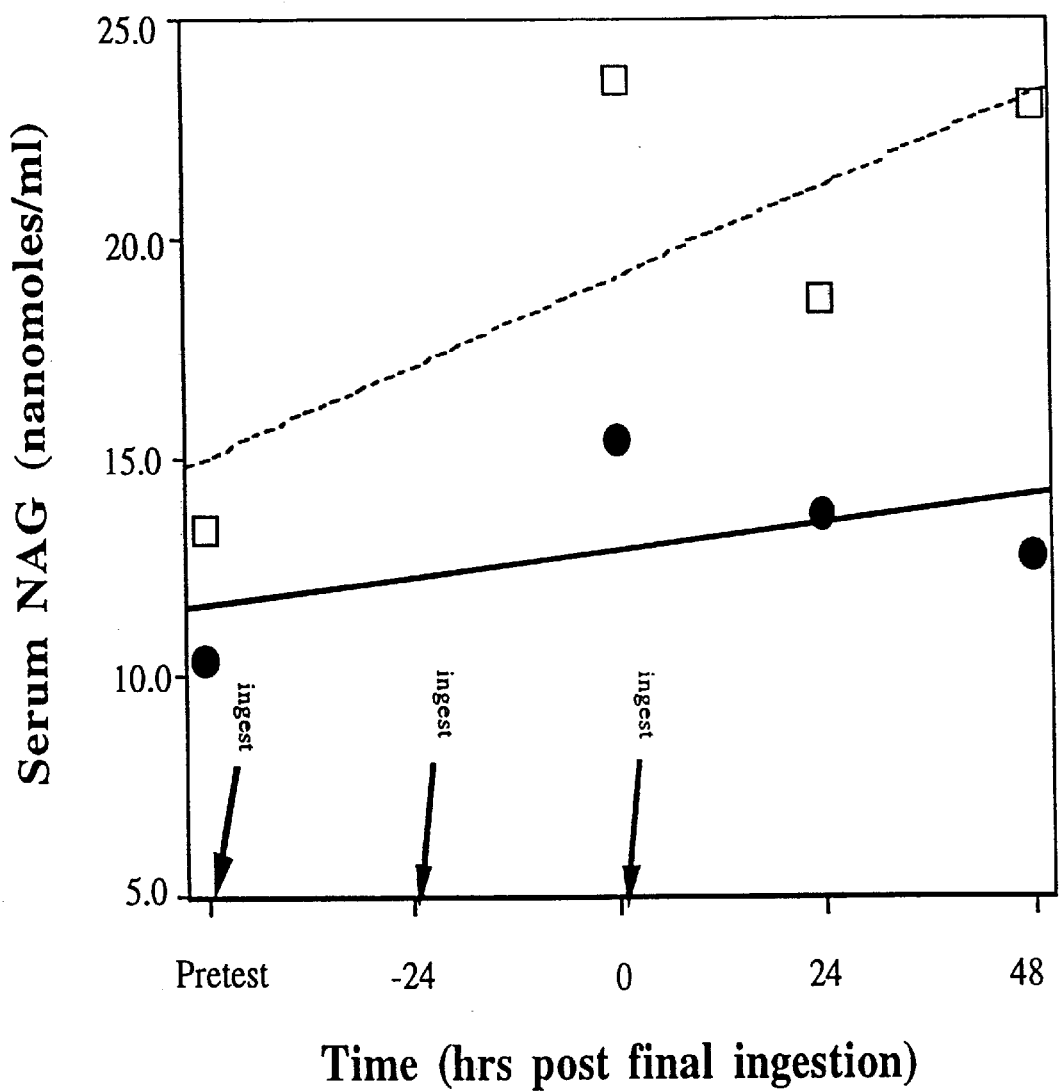
FIG. 1 is a chart illustrating the effect of the oral ingestion of NAG or poly-NAG on serum NAG levels. Blood sample values for subjects that ingested NAG are represented by closed circles. Blood sample values for the subjects that ingested poly-NAG are represented by open squares.

The methods of the present invention relate to administering to a mammal afflicted with osteoarthritis an effective amount of poly-N-acetyl-D-glucosamine (poly-NAG), partially depolimerized poly-NAG, pharmaceutically acceptable salts of poly-NAG, or mixtures thereof, to treat osteoarthritis and/or alleviate the symptoms of osteoarthritis such as pain, joint tenderness and swelling and impaired joint mobility.

The products of the present invention comprise solid and liquid pharmaceutical dosage forms for oral and by-injection administration comprising poly-NAG, its pharmaceutically acceptable salts and mixtures thereof. These dosage forms may be administered orally and by-injection to treat osteoarthritis and/or alleviate the symptoms thereof.

As used herein, poly-NAG refers to poly-N-acetyl-D-glucosamine, pharmaceutically acceptable salts of poly-N-acetyl-D-glucosamine, and mixtures thereof.

Poly-NAG is a polysaccharide, also known as chitin, which forms the cell walls of fungi and the hard cells of insects and crustaceans. Poly-NAG, is nontoxic and very inexpensive. It has now been surprisingly found that poly-NAG provides a longer lasting source of blood NAG (N-acetyl-D-glucosamine) in humans as compared to administration of comparable amounts of NAG. The NAG is known to degrade in the body of a mammal to glucosamine. This is a result of a slow degradation of poly-NAG which thus becomes a continuous source of NAG monomers, NAG dimers, other oligomers and glucosamine monomers. The fact that poly-NAG would be degraded in the blood to NAG and glucosamine was not readily apparent given that poly-NAG is highly resistant to chemical degradation.

Poly-NAG has been previously used in the form of ground chitin to promote wound healing as taught by Balassa in U.S. Pat. Nos. 3,632,754; 3,903,268; 3,911,116; and 3,914,413.

Poly-NAG used in the present invention may be naturally occurring (extracted from fungi or shells) or synthetic. Suitable natural sources of poly-NAG are from lobsters, shrimp and other crustacea as well as from fungal origin. The non-limiting examples of useful fungi that can be used as a useful source of chitin are *Mucor spinosus, Aspergillus niger*, Penicillium and Cryptococcus.

Methods of preparing natural chitin, i.e., poly-NAG, are taught by Balassa in U.S. Pat. Nos. 3,903,268; 3,911,116 and 3,914,413 and J. Ornum, *Infofish International*, 6:48–52 (1992).

Poly-NAG derivatives are also within the scope of the invention. The poly-NAG derivatives contemplated are materials such as ethers formed with pharmaceutically acceptable radicals and esters or salts with pharmaceutically acceptable acids. Examples of suitable derivatives include hydroxy lower alkyl poly-NAG such as hydroxyethyl poly-NAG, carboxy alkyl poly-NAG such as carboxymethyl poly-NAG, salts of carboxy lower alkyl poly-NAG such as the zinc salt, lower alkyl poly-NAG such as methyl poly-NAG and ethyl poly-NAG, poly-NAG acetate, poly-NAG nitrate, poly-NAG citrate, poly-NAG phosphate, N-acyl derivatives derived from monocarboxylic aliphatic acids such as N-formyl, N-acetyl, N-propionyl, N-caproyl, etc.

Combinations of the therapeutically effective agents described above with poly-NAG and/or poly-NAG derivatives may be administered to treat osteoarthritis according to the present invention. Pharmaceutical dosage forms containing these materials in combination with poly-NAG and its derivatives are within the scope of this invention.

To treat osteoarthritis and/or alleviate its symptoms, poly-NAG may be administered orally or by injection. Oral poly-NAG may be in the form of a liquid as a suspension, or alternatively in solid form as a tablet, pellet, powder or capsule. Poly-NAG may be also administered by injection, i.e., intravenously, intramuscularly, intra-articularly or subcutaneously in the form of a sterile suspension.

Liquid pharmaceutical dosage forms for oral administration of poly-NAG such as suspensions of poly-NAG in pharmaceutically acceptable liquids are within the scope of the invention and may be prepared according to conventional techniques well known in the art. Satisfactory pharmaceutically acceptable liquids include water, sugar suspensions, and aqueous glycols which may be compounded with coloring agents and synthetic or natural flavors.

Solid dosage forms for oral administration of poly-NAG, such as pellets, capsules, tablets or powder can also be used in practicing the present invention. The tablets and capsules may be prepared in accordance with conventional procedures in which poly-NAG is combined with the well known pharmaceutical excipients such as starch, sugar, bentonite clays, and other commonly used carriers.

To prepare dosage forms to be administered by injection it is necessary to prepare a dispersion of poly-NAG in a pharmaceutically acceptable liquid. Colloidal suspensions of poly-NAG may be prepared using the method described by Lingappa and Lockwood in Nature, 189:158 (1961). Aqueous dosage forms for subcutaneous, intravenous and intraarticular administration are prepared by admixing poly-NAG in a suitable sterile mixture of pharmaceutical materials commonly used for compounding injectable suspensions (preferably 1 to 10%). The sterile extract may contain preservatives such as methyl and/or propyl paraben.

Modifications of the above-described dosage forms for oral and by-injection administration of poly-NAG will be apparent to those skilled in the art and are considered to be within the scope of this invention.

The quantity of effective dose supplied by each capsule, tablet or injection is relatively unimportant since the total dosage can be reached by administration of either one or a plurality of liquid doses, capsules or tablets, or both, or by one or more injections.

The methods of the present invention relate to treatment and/or alleviation of the symptoms of osteoarthritis by administering orally or by injection a pharmaceutically effective amount of poly-NAG to a mammal in need of such treatment and/or suffering from such symptoms. The effective amount of administered poly-NAG depends upon the severity of condition, the stage of the disease and the individual inflammatory characteristics of a mammal being treated. Generally, an effective amount of poly-NAG administered orally is in the range from about 100 milligrams to about 10,000 milligrams of poly-NAG per day and preferably from about 100 to about 2,500 milligrams per day. It is especially preferred to administer about 1,500 mg per day. A preferred mode of oral administration of poly-NAG is in a solid oral dosage form (as a tablet, capsule or pellet) although aqueous suspensions or syrup formulations are employed with success.

An effective amount of poly-NAG administered by intravenous or subcutaneous injection is from about 100 to about 10,000 mg of poly-NAG a day and preferably from about 100 to about 1,000 mg per day. The effective amount for intraarticular injection is generally one tenth of the amount used for intravenous injection because poly-NAG is delivered directly to the affected joint.

The oral and by-injection administration may be combined in the same treatment. The treatment with poly-NAG can also be combined with other therapies for treating osteoarthritis or other degenerative skeletal diseases such as analgesics (narcotics and non-narcotics), commercial and experimental therapeutic agents as well as medical devices used for such treatments. Modifications of these regimens will be apparent to those skilled in the art.

Daily doses for both the oral and by-injection treatments can be administered once a day or a number of times per day.

The duration of the treatment by the compositions of the invention depends on the patients condition and will be apparent to those skilled in the art. For example, administration within the dosage levels described above may go on for between about 2 to about 8 weeks, and preferably from between about 4 to about 6 weeks. The treatment at these dosage levels is continued until there is a noticeable amelioration of the patient's condition at which time daily doses may be reduced by one half. Thus, a patient receiving the preferred oral dose of 500 milligrams per day would be treated at this dosage level until there was a noticeable (at least 25 % improvement) amelioration of symptoms (as measured by increased range of motion, i.e., joint mobility, decreased level of pain, decreased swelling in affected joints, decreased joint tenderness) at which time the patient's daily doses would be reduced to 250 mg of poly-NAG. The 250 mg/day dose would be continued until the patient's symptoms (i.e., joint tenderness, swelling etc.) went into remission. Treatments may be repeated as required by the patient's condition.

Given the detailed disclosure and guidance in the present specification, those skilled in the art can optimize, using routine testing, effective amounts of poly-NAG, administration regimens and the duration of treatment to suit the needs of individual patients. The mammals that may be treated with the present invention include humans as well as animals including cats, horses and dogs.

The dosage forms, effective amounts and administration schedules are generally the same for treating and alleviating the symptoms of osteoarthritis. Generally, the following symptoms are monitored: pain, joint tenderness and swelling, and joint mobility. The treatment is generally continued until at least one of the symptoms is alleviated, and then continued at a reduced dose until all symptoms are in remission. Given the detailed guidance in this specification, one skilled in the art would know how to optimize the invention to suit the individual patient's symptoms. Any such modifications are considered to be within the scope of this invention.

The following are non-limiting examples that show the manner of using poly-NAG to treat and/or alleviate symptoms of osteoarthritis.

EXAMPLE 1

Poly-NAG Increases Serum NAG Levels and Hydrolyses to Glucosamine in vivo

Ten normal, healthy subjects (five men and five women ages 36–50) were randomly divided into two groups (designated as A and B). On Day-1 a fasting blood sample was collected from each patient. Following this, group A orally ingested 1.0 gram of NAG and group B ingested 1.0 gram of poly-NAG. On Day-2 the subjects again ingested one gram of the appropriate test substance before breakfast. On the third day a fasting blood sample was taken at time T=0. Subsequently, they consumed the final 1.0 gram of the appropriate test substance, and nonfasting blood samples were taken at 1, 2, 4, and 8 hours. Fasting blood samples were taken at 24 and 48 hours thereafter. On Days 4–7 the subjects did not consume any of the test material, but continued their normal diets. On Day-8, after a fasting blood sampling, the groups were switched (i.e., group A took poly-NAG while group B consumed NAG) and the same procedure as shown above was repeated.

The data were analyzed using analytical HPLC procedure based on published methods for amino sugar analysis. The chromatographic system consisted of a Hewlett-Packard 1090M Liquid Chromatograph/Work Station equipped with a Diode Array Detector. Separation was by isocratic elution at 40° C. from a 300×7.8 mm Rezex Organic Acid Column (Phenomenex; N>75000 P/m) with 0.005N $H_2SO_4$ at a flow rate of 0.6 ml/min. The analytical conditions had been developed for resolution of the aminosugar/acetylated aminosugar components of physiological fluids, and the diode array detector was optimized at 193 nm for maximum sensitivity and minimum interference. The system was calibrated with standards before, during and after the study to assure there were no significant changes due to wear and tear or aging of the system. The chromatographic data were transferred to a spreadsheet and statistically tested with ANOVA (Single Factor, Two-Factor without Replication, Two-Factor with Replication) and paired T-tests.

Table 1 summarizes the concentrations of NAG in serum following ingestion of 1.0 g per day of either NAG or poly-NAG.

TABLE 1

| | NAG-Ingestors | | POLY-Nag-Ingestors | |
| --- | --- | --- | --- | --- |
| | (nanomoles per ml of serum) | | | |
| Time | Avg | ±SD | Avg | ±SD |
| Pre | 10.3 | 4.4 | 13.4 | 7.0 |
| T0 | 15.4 | 8.7 | 23.0 | 18.3 |
| T1 | 18.2 | 10.0 | 15.6 | 6.0 |
| T2 | 21.0 | 18.4 | 24.3 | 19.9 |
| T4 | 22.9 | 16.7 | 23.7 | 20.8 |
| T8 | 14.6 | 9.3 | 13.8 | 10.4 |
| T24 | 13.6 | 12.0 | 18.6 | 14.1 |
| T48 | 12.7 | 8.3 | 23.0 | 13.2 |

However, due to individual differences and because subjects were not fasting in the T=1 through T=8 hour periods, it is more informative to view the quantitative responses of each individual. For example, comparison of serum NAG levels at T=0 with the pretest values showed that 65% of the subjects (13/20) increased serum NAG concentrations. The NAG-ingestors and poly-NAG-ingestors were essentially equal (6/20 and 7/20, respectively). Since the T=0 sample was taken in the morning before taking the "final dose" of the drug, another important comparison was between the pretest value and the T=1 hour value. In this case, 70% of subjects (14/20) showed an increase in serum NAG (6/20 for poly-NAG ingestors and 8/20 for NAG ingestors). These data establish that ingestion of either NAG or poly-NAG results in absorption and elevation of serum NAG.

Upon cessation of ingestion of NAG or poly-NAG, the levels of serum NAG did not immediately return to the prior baseline levels (FIG. 1). At 24 hours following cessation of ingestion of either NAG or poly-NAG, only 20% of the subjects (4/20) showed decreased serum NAG levels. At 48 hours after ceasing the dietary supplement, 55% of the subjects still showed higher levels of serum NAG than at the pretest. These data show that clearance of the NAG is not complete by 48 hours. More importantly, when patients ingested poly-NAG as compared to NAG, the serum levels of NAG were at a higher level and remained elevated for a longer period of time in the patients that took poly-NAG. (FIG. 1).

Since glucosamine can arise from the hydrolysis (deacetylation) of NAG and is a normal breakdown product of NAG, serum glucosamine levels were also measured. The serum glucosamine levels during the washout period were elevated at 24 and 48 hours over the pretest values. For example, at 48 hours the serum glucosamine levels were elevated 10.2% and 12.8% over the pretest levels for the NAG-ingestors and poly-NAG ingestors, respectively. These data show that the orally administered NAG and poly-NAG are hydrolyzed to glucosamine prior to further metabolism or excretion.

The patients reported no side effects, the compliance with the protocol was maintained without problems and there were no differences in responses between males and females.

EXAMPLE 2

Treatment/Alleviation of Symptoms of Osteoarthritis by Oral Administration of poly-NAG Twenty patients with osteoarthritis are randomly divided in two groups designated as group A and group B. Group A is orally administered before breakfast three tablets comprising poly-NAG each containing 500 mg of poly-NAG. Poly-NAG is administered each day for a period of 6 weeks. No other analgesic, antirheumatic or anti-inflammatory drugs are administered at the same time. Group B is administered lactose placebo. Pain and joint swelling, tenderness and mobility are monitored in both groups and compared. The treatment is repeated as needed depending on the individual condition of each patient.

EXAMPLE 3

Treatment/Alleviation of Symptoms of Osteoarthritis by Intravenous Administration of poly-NAG Twenty patients with osteoarthritis are randomly divided in two groups designated as group A and group B. Group A is administered one injection a day containing 500 mg of poly-NAG. The treatment is repeated every day for a period of 6 weeks. No other analgesic, antirheumatic or anti-inflammatory drugs are administered at the same time. Group B is administered a saline solution. Pain and joint swelling, tenderness, and mobility are monitored in both groups and compared. The treatment is repeated as needed depending on the individual condition of each patient.

What is claimed is:

1. A method of treating osteoarthritis in mammals comprising administering to a mammal in need of such treatment an effective amount for treatment of osteoarthritis of a member selected from the group consisting of a poly-N-acetyl-D-glucosamine (poly-NAG), a pharmaceutically acceptable derivative of poly-NAG, and mixtures thereof.

2. The method according to claim 1, wherein said material is said poly-N-acetyl-D-glucosamine (poly-NAG).

3. The method according to claim 1, wherein said pharmaceutically acceptable derivative of poly-NAG is selected from the group consisting of hydroxy lower alkyl poly-NAG, carboxy lower alkyl poly-NAG, a salt of carboxy lower alkyl poly-NAG, lower alkyl poly-NAG, poly-NAG acetate, poly-NAG nitrate, poly-NAG citrate, and poly-NAG phosphate.

4. The method according to claim 1, which comprises administering said effective amount orally.

5. The method according to claim 1, which comprises administering said effective amount by injection.

6. The method according to claim 4, wherein said effective amount is between about 100 and about 10,000 mg/day.

7. The method according to claim 5, wherein said effective amount is between about 100 and about 10,000 mg/day.

8. The method according to claim 1, wherein said mammal is a human.

9. A method of alleviating the symptoms of osteoarthritis in mammals comprising administering to a mammal suffering from such symptoms a therapeutically effective amount of a material selected from the group consisting of a poly-N-acetyl-D-glucosamine (poly-NAG), a pharmaceutically acceptable derivative of poly-NAG, and mixtures thereof, to alleviate at least one of the symptoms of osteoarthritis.

10. The method according to claim 9, wherein said material is said poly-N-acetyl-D-glucosamine (poly-NAG).

11. The method according to claim 9, wherein said pharmaceutically acceptable derivative of poly-NAG is selected from the group consisting of hydroxy lower alkyl poly-NAG, carboxy lower alkyl poly-NAG, a salt of carboxy lower alkyl poly-NAG, lower alkyl poly-NAG, poly-NAG acetate, poly-NAG nitrate, poly-NAG citrate, and poly-NAG phosphate.

12. The method according to claim 9, which comprises administering said effective amount via the oral route.

13. The method according to claim 12, wherein said effective amount is between about 100 and about 10,000 mg/day.

14. The method according to claim 9, which comprises administering said effective amount in a solid dosage form.

15. The method according to claim 9, which comprises administering said effective amount by injection.

16. The method according to claim 9, wherein said mammal is a human.

* * * * *